United States Patent [19]

DeLuca et al.

[11] 4,260,804

[45] Apr. 7, 1981

[54] PROCESSES FOR PREPARING CALCITROIC ACID AND ESTERS THEREOF

[75] Inventors: Hector F. DeLuca; Heinrich K. Schnoes, both of Madison, Wis.; Robert P. Esvelt, Rice, Wash.

[73] Assignee: Wisconsin Alumni Research Foundation, Madison, Wis.

[21] Appl. No.: 122,921

[22] Filed: Feb. 20, 1980

[51] Int. Cl.³ .................... C07C 61/12; C07C 61/28; C07C 69/74
[52] U.S. Cl. .................................. 560/117; 562/499; 260/397.1
[58] Field of Search ...................... 260/397.1; 560/126, 560/117; 562/508, 499

[56] References Cited

U.S. PATENT DOCUMENTS 3,833,622  9/1974  Babcock et al. .................. 260/397.2

*Primary Examiner*—Elbert L. Roberts
*Attorney, Agent, or Firm*—Howard W. Bremer

[57] ABSTRACT

A method for chemically synthesizing calcitrioic acid and esters thereof. Calcitroic acid displays antirachitic (vitamin D-like) activity.

9 Claims, No Drawings

PROCESSES FOR PREPARING CALCITROIC ACID AND ESTERS THEREOF

The invention described herein was made in the course of work under a grant or award from the Department of Health, Education, and Welfare.

This invention relates to biologically active vitamin D compounds.

More specifically this invention relates to esters of calcitroic acid and to methods for their preparation.

Calcitroic acid is an in vivo metabolite of 1α,25-dihydroxyvitamin $D_3(1\alpha,25\text{-}(OH)_2D_3)$. This latter compound is the most potent known metabolite in the vitamin D series for the regulation of calcium and phosphate hemeostasis as fully documented in the literature (DeLuca and Schnoes, Ann. Rev. Biochem. 45, 631, 1976.) Recently it was discovered that rats rapidly metabolize $1\alpha,25\text{-}(OH)_2D_3$ to a compound having an acid function in the steroid side chain. This novel metabolite was isolated as the corresponding methyl ester and identified as methyl 1α,3β-dihydroxy-24-nor-9,10-seco-chola-5,7,10(19)-trien-23-oate depicted by structure $1(R=CH_3)$ for which the trivial name methyl calcitroate has been proposed (Esvelt et al, Biochemistry 18, 3977, 1979.) The in vivo metabolite is therefore the corresponding free acid, namely calcitroic acid as shown by structure $1(R=H)$ below. (An alternative trivial name for this compound is 1α-hydroxycalcioic acid.)

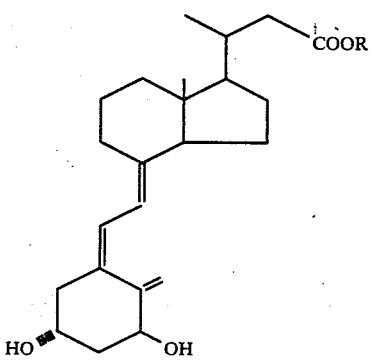

1: R = H calcitroic acid
R = CH₃ methyl calcitroate

A process for the chemical synthesis of calcitroic acid and of esters thereof has now been developed. The general process is outlined in Process Schematic 1, and is further described by the specification and examples which follow.

In this specification and in the claims the term "alkyl" denotes a lower alkyl radical of from 1 to about 5 carbons which may be of straight chain or branched chain configuration (e.g. methyl, ethyl, butyl, isopropyl, isobutyl, etc.) and the term acyl denotes an aliphatic acyl group of from 1 to about 5 carbons, such as formyl, acetyl, propionyl, butyryl, or an aromatic acyl groups such as benzoyl or substituted benzoyl, e.g. toluoyl, nitrobenzoyl or halobenzoyl. Arabic numerals identifying specific intermediates and products in this specification or in the specific examples refer to structures so numbered in the following Process Schematic.

The process uses commercially available acid 2 (where R is a hydroxy-protecting group, e.g. acyl, tetrahydropyranyl, methoxymethyl, alkylsilyl) as starting material which by an Arndt-Eistert homologation sequence using the general method of Ryer and Gebert (J. Am. Chem. Soc. 74, 43, 1959) gives the side chain desired in the final product. Use of methanol in the silver oxide-catalyzed Wolff rearrangement gives the methyl ester 3(R=acyl) in about 60% yield after recrystallization. Ester 3 is converted to diene 4a, by allylic bromination and dehydrobromination according to well-known procedures (Hunziker and Mullner, Helv. Chim. Acta 41, 70, 1958; Napoli et al Arch. Biochem. Biophys. 197, 119, 1979). Removal of the hydroxy-protecting group (e.g. by mild acid or base hydrolysis, depending on the protecting group present, and according to well-known procedures) yields the hydroxy ester 4b(R=CH₃). More vigorous basic hydrolysis (e.g. 10% NaOH/dil. methanol, 60–100° C., 1–3 hr.) also cleaves the ester function to give the acid (4b, R=H) and from this acid other alkyl esters are readily prepared, if desired. For example, esterification of the acid or the acid halide with any desired low molecular weight alcohol according to procedures well known in the art, yields other alkyl or aryl esters suitable for subsequent interconversions (e.g. 4b where R is lower alkyl such as methyl, ethyl, propyl, butyl, or a benzyl group). Irradiation of ester 4b (R=alkyl) with ultraviolet light yields the previtamin ester 5(R=alkyl), which is isomerized by heating (60–80° C.) in an alcohol or benzene solvent to the vitamin ester 6(R=alkyl). Alternatively, ester 6(R=alkyl) can, of course, also be obtained by subjecting the 3-O-protected derivatives of the 5,7-diene intermediate of general structure 4b to the irradiation/thermal isomerization sequence described above, to give the 3-O-protected derivative of ester 6. Subsequent removal of the protecting group yields hydroxy ester 6. The free acid (compound 6, R=H) is readily obtained from the ester (6, R=alkyl) by vigorous base hydrolysis (e.g. 10%NaOH, eq. alcohol, 1–3 hr, 60–90° C.) and from the acid the corresponding 3-O-protected derivatives are readily prepared, if desired, by standard procedures. The 3-O-acylates are preferred derivatives.

Introduction of the 1α-hydroxy function is achieved by the method of Paaren et al (Proc. Nat. Acad. Sci. USA 75, 2080, 1978). Ester 6 (R=alkyl) is converted to the cyclovitamin ester 7, by a two-step process involving tosylation of 6 to the 3-O-tosyl derivative followed by bicarbonate buffered methanolysis of the tosylate (Paaren et al, supra; Sheves and Mazur, J. Am. Chem. Soc. 97, 6249, 1975). Subsequent allylic oxidation of 7(R=alkyl) with selenium dioxide and T-butyl hydroperoxide in a halocarbon solvent yields the desired 1α-hydroxy cyclovitamin ester 8(R=alkyl). Vigorous base hydrolysis of either 7 or 8 (where R=alkyl) using conditions as described for ester 6 provides the corresponding free acids. The 1-hydroxy group of ester 8 (R=alkyl) can be protected (e.g. by acyl, tetrahydropyranyl, methoxy-methyl, alkylsilyl groups) using standard derivatization,conditions, the 1-O-acylates (e.g. acetyl, formyl,,benzoyl) being preferred derivatives. The 1-O-acylates can be subjected to acid catalyzed solvolysis (e.g. using formic, acetic or paratoluene sulfonic acid) as described by Paaren et al (supra.) to yield either 1,3-di-O-acyl-, or 1-O-acyl-3-hydroxyvitamin D esters, depending upon the solvolysis conditions chosen, as a mixture of the 5,6-cis and 5,6-trans-isomers. For example, solvolysis in carboxylic acids (e.g. formic or acetic acid) leads to 1,3-di-O-acylates where the C-3 acyl group corresponds to the acyl moiety of the acid used, whereas solvolysis with sulfonic acids in aqueous media yields 1-0-acyl-3-hydroxy-products, as fully described by Paaren et al. After separation of the 5,6 cis and trans mixture, the 5,6-cis product is hydrolyzed in mild alkali to yield the desired calcitroic acid ester (compound 1, R=alkyl).

A preferred procedure consists of the direct solvolysis of unprotected hydroxy ester 8 with a low molecular weight carboxylic acid (acetic acid being a preferred acid) to give 1α-hydroxyvitamin D ester 3-0-acyl (9, R=alkyl) and the corresponding 5,6-trans-isomer (1α-hydroxy-5,6-transvitamin D ester 3-0-acyl) in a mixture ratio of ca. 3:1. These isomers are readily separated by chromatography (e.g. high pressure liquid chromatography, thin layer chromatography). Mild basic hydrolysis of 9 (R=alkyl) then yields the desired calcitroic acid ester 1 (R=alkyl). Vigorous alkaline hydrolysis of the ester (e.g. 10% NaOH, dilute alcohol, 60–100° C., 1–3 hr.) provides the corresponding acid, calcitroic acid, compound 1 (R=H), in pure form.

Acylated derivatives of these calcitroic acid esters (compounds of structure 1, R=alkyl) with 1-0-acyl or 1,3-di-0-acyl groups are obtained by the use of alternative solvolysis conditions as described above or by acylation of intermediate 9 to the corresponding 1,3-di-0-acyl derivative (where the acyl groups may be the same or different) using well known acylation procedures. Similarly the 1,3-di-0-acyl derivatives of calcitroic acid (1, R=H) are readily obtained by direct acylation of this acid. If calcitroic acid or its esters are desired with other 1,3-0-protecting groups, such groups may be conveniently selected from tetrahydropyranyl, methoxymethyl or alkylsilyl.

The 5,6-trans intermediates obtained after solvolysis of the cyclovitamin intermediate (e.g. compound 9 with 5,6-trans double bond configuration) are converted by hydrolysis of the acyl group to 5,6-trans calcitroic acid esters and further hydrolysis of the ester yields 5,6-trans calcitroic acid. These hydrolysis steps are conducted exactly as described for the 5,6-cis compounds. Any of these 5,6-trans intermediates or products are of course convertible to the corresponding natural 5,6-cis compound, by the well-known photochemical isomerization process of Inhoffen et al, Chem. Ber. 90, 2544 (1957). For the following specific examples NMR were taken in CDCl$_3$ with a Bruker WH-270 FT spectrometer. Mass spectra were obtained at 110–112° C. above ambient at 70 eV with an AEI MS-9 spectrometer coupled to a DS-60 data system. Ultraviolet (UV) absorption spectra were recorded in methanol with a Beckman Model 24 recording spectrophotometer. HPLC was performed on a Waters Associates Model ALC/GPC 204 using Zorbax-SIL (Dupont) 6.4 mm×25 cm or 4.8 mm×25 cm columns monitoring at 313 nm for preparative samples or 254 nm for analytical samples. Liquid scintillation counting of radioactivity was determined with a Packard model 3255 using a scintiallation solution consisting of 0.4%2,5-diphenyl oxazole and 0.03% dimethyl-1,4-bis(2(5-phenyloxazolyl)) benzene in toluene. All reactions are preferably conducted under an inert atmosphere.

EXAMPLE I

Methyl 3β-acetoxy-24-nor-5-cholen-23-oate (3, R=acetyl).

A solution of 5 g (12.3 nm) of 2 (R=acetyl) in 10 ml of freshly distilled thionyl chloride was stirred at 25° C. for 90 min. Excess thionyl chloride was removed by distillation following 5 additions of 20 ml benzene. The brown residue was suspended in 50 ml benzene and slowly added to a 130 ml ether solution containing approximately 2 g of diazomethane (2-fold excess) at 0° C. The reaction mixture was left at room temperature for 18 h resulting in the formation of pale yellow crystals. Solvents were evaporated and the crude diazoketone, dissolved in 50 ml benzene and 110 ml methanol, was heated to 60° C. and a suspenson of 6 mmoles silver oxide in 50 ml methanol was added slowly. After refluxing at 70° C. for 20 h the solvents were evaporated and the residue (taken up in ether) was filtered through Celite. The ether solution was adjusted to 100 ml and washed with 0.1 NHCl, dilute NaHCO$_3$, water, and dried over sodium sulfate. The methyl ester product, 3 (R=acetyl), was recrystallized from 10% acetone in methanol and 100% ethanol to give 3.2 g (60%) of white needles. mp 126.0–127.2° C.; mass spectrum m/e (rel. int.) 356 (100M+-HOAc), 341 (29), 325 (2.4), 282 (4.5), 255 (24); nmr (CDCl$_3$) δ0.66 (s, 3H, 18-CH$_3$), 0.93 (d, 3H, 21-CH$_3$) 0.97 (s, 3H, 19-CH$_3$), 2.01 (s, 3H, -OAc), 2.27 (d, 2H, 22-CH$_2$), 3.60 (s, 3H, OACMe), 4.5 (m, 1H, 3α-H), 5.33 (m, 1H, 6-H).

EXAMPLE 2

Methyl 3β-hydroxy-24-norchola-5,7-dien-23 -oate (4b, R=CH$_3$).

To a solution of 3 (R=acetyl) (500 mg, 1.2 mmoles) in 22 ml benzene and 17 ml hexane was added 500 mg NaHCO$_3$ and 1.5 eg. 1,3-dibromo-5,5-dimethyl-hydantoin. The reaction mixture was refluxed at 75° C. for 20 min then rapidly cooled and filtered. The residue obtained upon solvent evaporation was dissolved in 17 ml xylene and 4 ml s-collidine and refluxed for 90 min. Ether was added and the organic phase was thoroughly washed with 1 N HCl, dilute NaHCO$_3$, water, saturated NaCl, and then dried over Na$_2$SO$_4$. The residue (containing 5,7- and 4,6-diene products) was heated in dry dioxane with 80 mg p-toluene sulfonic acid at 70° C. for 35 min. The mixture was diluted with ether and washed with water, dilute bicarbonate, water and saturated NaCl. The dried residue was chromatographed on a silica gel column (2×15 cm) eluted with 15% EtOAc in hexane. The product (4a) (R=acetyl) eluting between 51 and 102 ml obtained in 29% yield from 3 was stirred in 10 ml ether and 10 ml 5% (w/v) KOH in 95% methanol for 30 min at room temperature. The reaction mixture was diluted with ether and the organic phase washed as above. The product was purified by tlc (40% EtOAc in hexane, developed twice, Rf 0.33) to give 96 mg of 4b (R=CH$_3$) (21% from 3). Uvλ$_{max}$262, 271, 282, 292, nm. High resolution mass spectrum, calc'd. for C$_{24}$H$_{36}$O$_3$: 372.2664; found: 372.2652. nmr δ0.66 (s, 3H, 18-CH$_3$), 0.94 (s, 3H, 19-CH$_3$), 1.01 (d, 3H, 21-CH$_3$), 3.67 (s, 3H, COOCH$_3$), 2.76 (m, 1H, 3α-H), 5.39 (d, 1H, 7-H), 5.56 (d, 1H, 6-H).

EXAMPLE 3

Methyl 3⊖-hydroxy-24-nor-9,10-seco-chola-5,7,10(19)trien-23-oate (6) (R=CH$_3$).

Ether solutions of approximately 20 mg of 4b (R=CH$_3$) were irradiated on ice and under nitrogen for 10 min with a mercury arc lamp (Hanovia 9A-1) fitted with a Corex filter. The residues obtained after solvent evaporation were chromatographed on HPLC (6.4 mm×25 cm Zorbax-SIL, 4 ml/min 1500 psi) eluted with 1.5% 2-propanol in hexane. Pure previtamin, 5, (R=CH$_3$) was collected at 45 ml (UV:$\lambda_{max}$260 nm $\lambda_{min}$231 nm). The combined previtamin containing fractions were heated in 10 ml ethanol at 80° C. for 150 min to yield 10.8 mg of 6 (R=CH$_3$) (11% yield from 4). UV, $\mu_{max}$264nm, $\mu_{min}$228 nm. High resolution mass spectrum calc'd. for C$_{24}$H$_{36}$O$_3$:372.2664; found: 372.2661; m/e (rel. int.) 372 (44), 354 (3), 341 (6), 313 (4), 298 (1), 271 (4), 253 (7), 136 (97), 118 (100). nmr $\delta$0.58 (s, 3H, 18-CH$_3$), 0.99 (d, 3H, 21-CH$_3$), 3.67 (s, 3H, COOCH$_3$) 3.95 (m, 1H, 3$\alpha$-H), 4.81 (s, 1H, 19(Z)-H), 5.05 (s, 1H, 19(E)-H) 6.03 (d, 1H, 7-H), 6.23 (d, 1H, 6-H).

EXAMPLE 4

Methyl 1$\alpha$,3$\beta$-dihydroxy-24-nor-9,10-seco-5,7,10(19)-chola-trien-23oate (calcitroic acid methyl ester, 1, R=CH$_3$).

A solution of 6 (R=CH$_3$) (10.2 mg, (27 umoles) in pyridine (0.2 ml) was treated with 30 mg p-toluene sulfonyl chloride at 4° for 22 hr. After addition of dilute bicarbonate (2 ml) the product was extracted with CHCl$_3$ ether (10 ml); the combined organic phases were washed with 1 N HCl, dilute bicarbonate, water, and saturated NaCl and dried over MgSO$_4$. The 3-tosyl derivative was then solvolyzed in 0.3 ml benzene, 2 ml methanol, and 50 mg NaHCO$_3$, heated to 56° C. for 18 hr. The resulting cyclovitamin product (7) (R=CH$_3$) was extracted into ether, washed with water and saturated NaCl, dried, and purified on silical gel tlc (30% EtOAc/hexane, Rf 0.54). This product in 0.7 ml CH$_2$Cl$_2$ was then added to an ice-cooled solution containing 0.5 eg. SeO$_2$ and 2 eq. t-BuOOH in 0.5 ml CH$_2$Cl$_2$. The reaction, followed by tlc, was allowed to proceed at room temperature for a total of 40 min and was stopped with the addition of NaHCO$_3$ and ether. The organic phase was washed with dilute bicarbonate, water, and saturated NaCl, and dried over MgSO$_4$. Evaporation of solvent gave 1$\alpha$-hydroxy derivative 8, (R=CH$_3$) which was dissolved in 0.5 ml glacial acetic acid and heated at 55° for 15 min. Products (9, R=CH$_3$) and the corresponding 5,6-trans isomer in ca 3:1 ratio) were extracted with ether, and the ether phase was washed as before. Compound 9 (R=CH$_3$) was purified by tlc (50% EtOAc in hexane rf. 0.32) followed by HPLC, (6.4×250 mM column, 2.5% of 2-propanol in hexane, at 2 ml/min and 900 psi). Product 9 (R=CH$_3$) eluting at 63 ml, was recycled through the column and obtained in pure form in 7.1% yield from 6 (UV$\lambda_{max}$264,$\lambda_{min}$228 nm). Mild hydrolysis of 9 (75 $\mu$l 0.1 M KOH/MeOH and 200 $\mu$l ether, 15°, 60 min) provided 1 (R=CH$_3$); UV$\mu_{max}$264 nm, $\mu_{min}$228 nm; high resolution mass spectrum: calc'd for C$_{24}$H$_{36}$O$_4$388.2614; found 388.2645; m/e (rel. int.) 388 (18), 370 (61), 357 (3), 352 (24), 314 (1), 287 (1), 269 (4), 251 (7), 152 (31), 134 (100); nmr $\delta$0.58 (s, 3H, 18 CH$_3$), 0.99 (d, 3H, 21 CH$_c$), 3.67 (s, 3H, COOCH$_3$), 4.23 (m, 1H, 3$\alpha$-H), 4.43 (m, 1H, 1$\beta$-H), 5.00 (s, 1H, 19(Z)-H) 5.33 (s, 1H, 19(E)-H), 6.02 (d, 1H, 7-H), 6.38 (d, 1H, 6-H).

EXAMPLE 5

Calcitroic acid (1, R=H).

Hydrolysis of 1 (R=CH$_3$) in 10% KOH/90% methanol at 60° C. for 30 min followed by neutralization and filtration in 100% ethanol gives quantitative yields (by tlc and UV) of the natural product 1 (R=H). UV$\lambda_{max}$264,$\lambda_{min}$228 nm.

EXAMPLE 6

Comparison with biologically generated 1 (R=CH$_3$).

The low resolution mass spectrum and the UV spectrum for synthetic 1 (R=CH$_3$) were identical with the spectra obtained for the methylated metabolite isolated from 1,25-(OH)$_2$D$_3$-treated rats (Esvelt et al, supra). (Direct comparison of nmr spectra was not possible because the low quantities of available natural product precluded nmr measurements). To confirm chromatographic identity, (3$\alpha$-$^3$H)-calcitroic acid was obtained from the livers of rats dosed with 1$\alpha$,25-dihydroxy(3$\alpha$-$^3$H)D$_3$, and converted to its methyl ester (1) (R=CH$_3$) as described by Esvelt et al (supra). This material (6500 dpm) was combined with 2 $\mu$g of synthetic 1 (R=CH$_3$) and the mixture was chromatographed on HPLC using the 4.6 mm column eluted with 8% 2-propanol in hexane, and the absorbance was monitored at 254 nm. Fractions were collected, evaporated, and counted. Radioactivity co-eluted exactly with the UV-absorbing peak due to synthetic 1 (R=CH$_3$) (elution volume, 40 ml). Spectral and chromatographic properties establish the identity between synthetic 1 (R=CH$_3$) and the methylated natural product.

Process Schematic 1

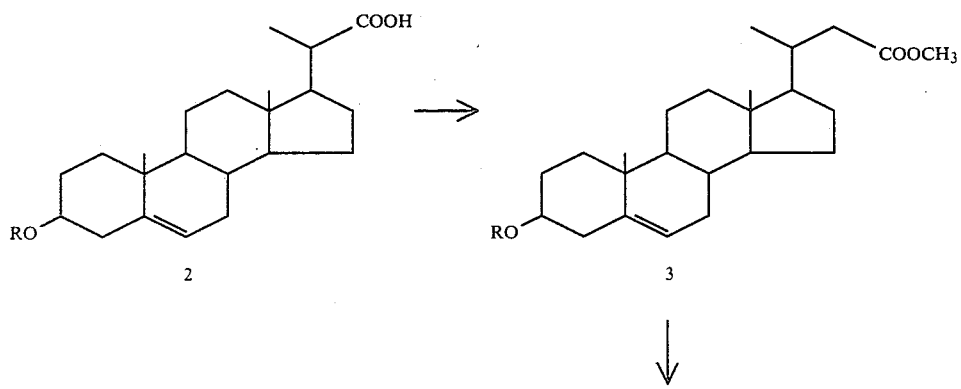

-continued
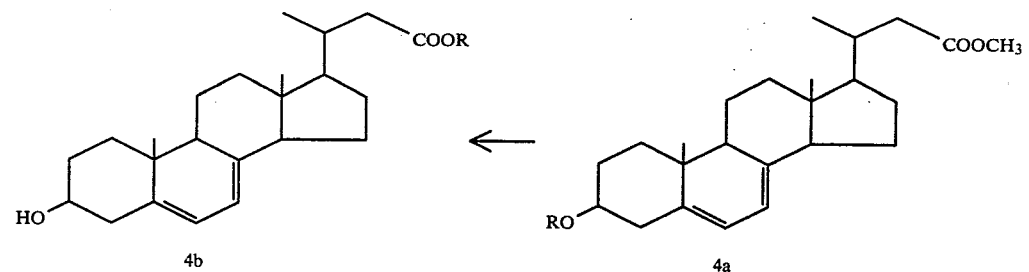
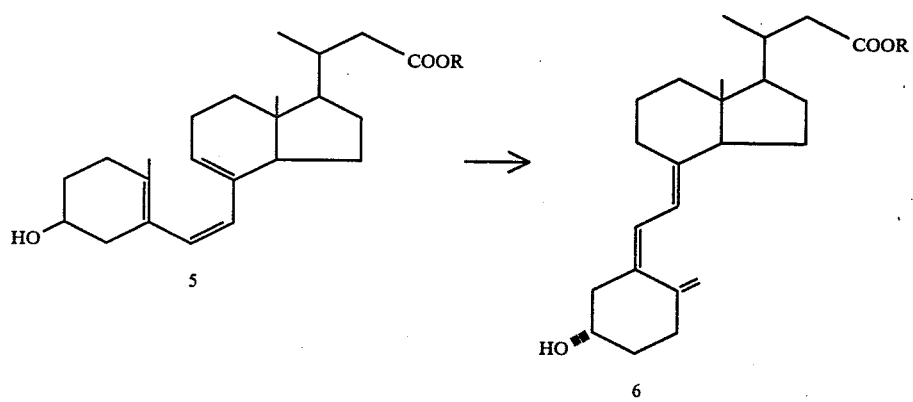
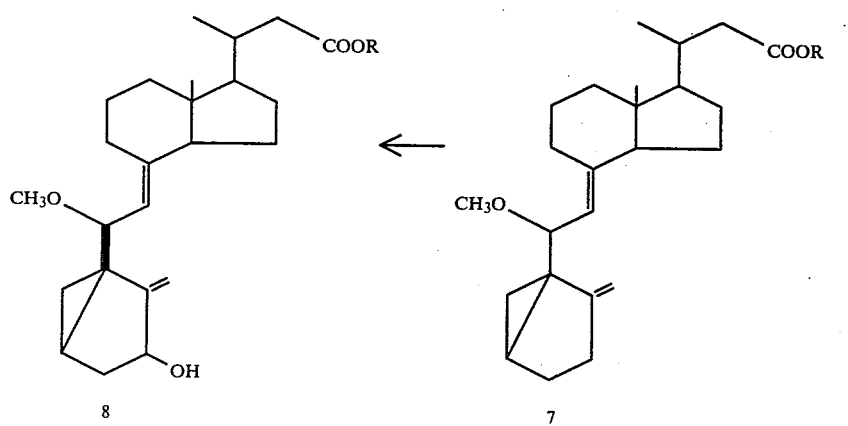

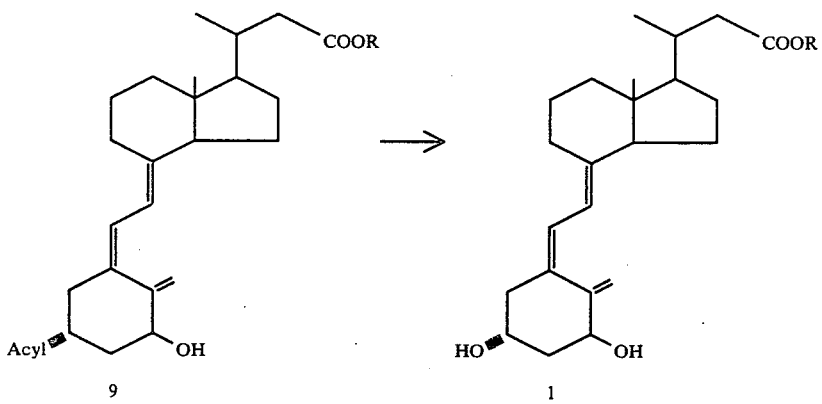

Having thus described the invention, what is claimed is:

1. Compounds having the formula

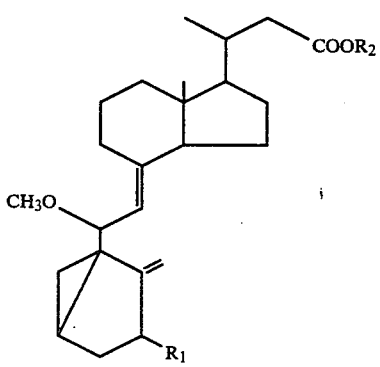

where $R_1$ is selected from the group consisting of hydrogen, hydroxy, O-acyl, O-methoxymethyl, O-alkylsilyl or O-tetra-hydropyranyl and where $R_2$ is hydrogen, alkyl or benzyl.

2. The compounds of claim 1 where $R_1$ is hydrogen.
3. The compounds of claim 1 where $R_1$ is hydroxy.
4. Compounds having the formula

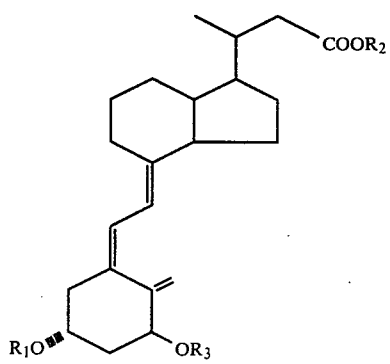

where each of $R_1$ and $R_3$, which may be the same or different is selected from acyl, tetrahydropyranyl, methoxymethyl and alkylsilyl and where $R_2$ is hydrogen, alkyl or benzyl.

5. The compounds of claim 4 where each of $R_1$ and $R_3$ is acyl.
6. Compounds having the formula

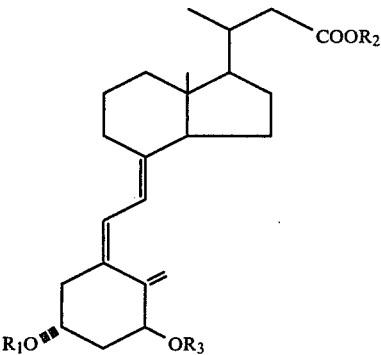

where $R_1$ and $R_3$ is selected from hydrogen or acyl, such that when $R_1$ is hydrogen, $R_3$ is acyl and when $R_3$ is hydrogen, $R_1$ is acyl, and where $R_2$ is hydrogen, alkyl or benzyl.

7. The compounds of claim 6 where the acyl group is acetyl.
8. Compounds having the formula

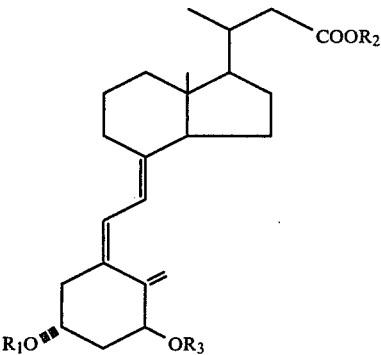

where each of $R_1$ and $R_3$ which may be the same or different, is selected from hydrogen, acyl, methoxymethyl, tetrahydro-pyranyl, and alkylsilyl and where $R_2$ is hydrogen, alkyl, or benzyl.

9. The compounds of claim 8 where $R_1$ and $R_3$ are selected from hydrogen or acyl.

* * * * *

UNITED STATES PATENT OFFICE
CERTIFICATE OF CORRECTION

Patent No. 4,260,804    Dated April 7, 1981

Inventor(s) Hector F. DeLuca et al

It is certified that error appears in the above-identified patent and that said Letters Patent are hereby corrected as shown below:

In Column 2, line 51, "T-butyl" should be -- t-butyl --

In Column 3, line 47, "CDC11$_3$" should be --CDCl$_3$--

In Column 4, line 60, "3$\Theta$" should be --3$\beta$--

In Column 5, line 5, "$\mu_{max}$264nm, $\mu_{min}$ 228 nm" should be --$\lambda_{max}$264nm, $\lambda_{min}$228 nm--

In Column 5, line 17, "umoles" should be --$\mu$moles--

In Column 6, line 5, UV$\mu_{max}$264 nm, $\mu_{min}$228 nm;" should be --UV$\lambda_{max}$264 nm, $\lambda_{min}$ 228 nm;--

In Column 6, line 9, "(d, 3H, 21 CH$_c$)" should be --(d, 3H, 21 CH$_3$)--

Signed and Sealed this

Twenty-third Day of June 1981

[SEAL]

Attest:

RENE D. TEGTMEYER

Attesting Officer     Acting Commissioner of Patents and Trademarks